United States Patent
Wu et al.

(10) Patent No.: US 11,986,629 B2
(45) Date of Patent: May 21, 2024

(54) PERSONALIZED CLOSED LOOP OPTIMIZATION SYSTEMS AND METHODS

(71) Applicant: MEDTRONIC MINIMED, INC., Northridge, CA (US)

(72) Inventors: Di Wu, Glendale, CA (US); Benyamin Grosman, Valley Village, CA (US); Louis J. Lintereur, Stevenson Ranch, CA (US); Anirban Roy, Agoura Hills, CA (US); Neha J. Parikh, West Hills, CA (US); Patrick E. Weydt, Moorpark, CA (US); Ali Dianaty, Porter Ranch, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 775 days.

(21) Appl. No.: 16/438,407

(22) Filed: Jun. 11, 2019

(65) Prior Publication Data

US 2020/0390973 A1    Dec. 17, 2020

(51) Int. Cl.
*G16H 20/10*    (2018.01)
*A61M 5/172*    (2006.01)
(Continued)

(52) U.S. Cl.
CPC .......... *A61M 5/1723* (2013.01); *G16H 10/40* (2018.01); *G16H 20/10* (2018.01); *G16H 20/17* (2018.01);
(Continued)

(58) Field of Classification Search
CPC ........ G16H 10/00; G16H 10/40; G16H 20/00; G16H 20/10; G16H 20/17; G16H 20/60;
(Continued)

(56) References Cited

U.S. PATENT DOCUMENTS 4,562,751 A    1/1986    Nason et al.
4,685,903 A    8/1987    Cable et al.
(Continued)

FOREIGN PATENT DOCUMENTS

AU    2019260574 A1    10/2020
CA    3107454 A1    10/2019
(Continued)

OTHER PUBLICATIONS

Wang, et al., Model Predictive Control for Type 1 Diabetes Based on Personalized Linear Time-Varying Subject Model Consisting of both Insulin and Meal Inputs: in Silico Evaluation, 2015 American Control Conference, Jul. 1-3, 2015. Chicago, IL, USA, 6 pages (Year: 2015).*

(Continued)

*Primary Examiner* — Jason S Tiedeman
(74) *Attorney, Agent, or Firm* — Weaver Austin Villeneuve & Sampson LLP

(57) ABSTRACT

A medical device system and related methods of automatically adjusting control parameters of a medical device are disclosed. One method involves obtaining data pertaining to a physiological condition of a patient during operation of the medical device in accordance with the operating mode, determining a plurality of adjusted values for the control parameter based at least in part on the data, determining a respective cost associated with each respective adjusted value for the control parameter based at least in part on the data using a cost function, identifying, from among the plurality of adjusted values, an optimized value from among the plurality of adjusted values, wherein the optimized value has a minimum cost associated therewith from among the plurality of costs, and updating the control parameter at the medical device to the optimized value.

15 Claims, 6 Drawing Sheets

(51) Int. Cl.
  *G16H 10/40* (2018.01)
  *G16H 20/17* (2018.01)
(52) U.S. Cl.
  CPC .............. *A61M 2205/3569* (2013.01); *A61M 2205/3584* (2013.01); *A61M 2205/502* (2013.01); *A61M 2205/52* (2013.01); *A61M 2230/201* (2013.01)
(58) Field of Classification Search
  CPC ........ G16H 40/00; G16H 40/60; G16H 40/63; A61M 5/1723; A61M 2205/3569; A61M 2205/3584; A61M 2205/502; A61M 2205/52; A61M 2230/201; A61M 5/14216; A61M 5/14244
  USPC ........................................................ 705/2, 3
  See application file for complete search history.

(56) References Cited

U.S. PATENT DOCUMENTS

| | | | |
|---|---|---|---|
| 4,755,173 A | 7/1988 | Konopka et al. | |
| 5,080,653 A | 1/1992 | Voss et al. | |
| 5,097,122 A | 3/1992 | Colman et al. | |
| 5,391,250 A | 2/1995 | Cheney, II et al. | |
| 5,485,408 A | 1/1996 | Blomquist | |
| 5,505,709 A | 4/1996 | Funderburk et al. | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,088,608 A | 7/2000 | Schulman et al. | |
| 6,119,028 A | 9/2000 | Schulman et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 | 7/2003 | Connelly et al. | |
| 6,591,876 B2 | 7/2003 | Safabash | |
| 6,641,533 B2 | 11/2003 | Causey, III et al. | |
| 6,659,980 B2 | 12/2003 | Moberg et al. | |
| 6,736,797 B1 | 5/2004 | Larsen et al. | |
| 6,740,072 B2* | 5/2004 | Starkweather ...... | A61M 5/1723 604/67 |
| 6,749,587 B2 | 6/2004 | Flaherty | |
| 6,752,787 B1* | 6/2004 | Causey, III ........... | A61M 5/172 604/152 |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,827,702 B2* | 12/2004 | Lebel ................ | A61M 5/14276 604/67 |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,323,142 B2 | 1/2008 | Pendo et al. | |
| 7,399,277 B2 | 7/2008 | Saidara et al. | |
| 7,402,153 B2 | 7/2008 | Steil et al. | |
| 7,442,186 B2 | 10/2008 | Blomquist | |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,474,332 B2 | 7/2013 | Bente, IV | |
| 8,674,288 B2 | 3/2014 | Hanson et al. | |
| 9,526,834 B2 | 12/2016 | Keenan et al. | |
| 9,907,909 B2* | 3/2018 | Finan .................... | G16H 20/17 |
| 11,147,919 B2 | 10/2021 | Parikh et al. | |
| 11,158,413 B2 | 10/2021 | Grosman et al. | |
| 11,367,526 B2* | 6/2022 | Chiu .................... | G16H 10/60 |
| 2002/0193679 A1 | 12/2002 | Malave et al. | |
| 2007/0123819 A1 | 5/2007 | Mernoe et al. | |
| 2008/0262745 A1 | 10/2008 | Polidori | |
| 2008/0269714 A1 | 10/2008 | Mastrototaro et al. | |
| 2009/0164239 A1 | 6/2009 | Hayter et al. | |
| 2010/0160861 A1 | 6/2010 | Causey, III et al. | |
| 2010/0249561 A1 | 9/2010 | Patek et al. | |
| 2011/0130746 A1 | 6/2011 | Budiman | |
| 2011/0208156 A1 | 8/2011 | Doyle, III et al. | |
| 2013/0030358 A1 | 1/2013 | Yodfat et al. | |
| 2013/0190583 A1* | 7/2013 | Grosman ............... | G16H 50/20 600/365 |
| 2013/0231642 A1* | 9/2013 | Doyle, III ........... | A61M 31/002 604/890.1 |
| 2013/0338630 A1 | 12/2013 | Agrawal et al. | |
| 2014/0066889 A1 | 3/2014 | Grosman et al. | |
| 2014/0066892 A1 | 3/2014 | Keenan et al. | |
| 2014/0128705 A1 | 5/2014 | Mazlish | |
| 2014/0200559 A1* | 7/2014 | Doyle, III .............. | G16H 20/10 604/891.1 |
| 2014/0276554 A1* | 9/2014 | Finan ................ | A61M 5/14244 604/504 |
| 2014/0276555 A1* | 9/2014 | Morales .............. | A61M 5/1782 702/19 |
| 2015/0057807 A1* | 2/2015 | Mastrototaro .......... | G16Z 99/00 700/275 |

(56) References Cited

U.S. PATENT DOCUMENTS

| | | |
|---|---|---|
| 2015/0352282 A1 | 12/2015 | Mazlish |
| 2016/0030339 A1 | 2/2016 | Muhlen-Bartmer et al. |
| 2016/0162662 A1 | 6/2016 | Monirabbasi et al. |
| 2017/0056591 A1 | 3/2017 | Breton et al. |
| 2017/0143899 A1* | 5/2017 | Gondhalekar ........ A61M 5/142 |
| 2017/0332952 A1* | 11/2017 | Desborough .......... G16H 20/17 |
| 2018/0020988 A1* | 1/2018 | Patek ................... A61B 5/7275 600/365 |
| 2018/0099092 A1* | 4/2018 | Roy ..................... A61M 5/142 |
| 2018/0174675 A1 | 6/2018 | Roy et al. |
| 2018/0200439 A1 | 7/2018 | Mazlish et al. |
| 2018/0200441 A1* | 7/2018 | Desborough ...... A61B 5/14532 |
| 2018/0286518 A1* | 10/2018 | Raju ...................... G16H 30/40 |
| 2018/0296757 A1 | 10/2018 | Finan et al. |
| 2019/0005195 A1* | 1/2019 | Peterson ................ G16H 50/20 |
| 2019/0258904 A1* | 8/2019 | Ma ........................ G06K 9/6269 |
| 2019/0336684 A1* | 11/2019 | O'Connor .............. G16H 20/17 |
| 2020/0093988 A1* | 3/2020 | Zhong ................. A61M 5/1723 |
| 2020/0098463 A1* | 3/2020 | Arunachalam ..... A61M 5/1723 |
| 2020/0098464 A1* | 3/2020 | Velado ................. A61B 5/4839 |
| 2020/0098465 A1* | 3/2020 | Jiang ....................... G16H 20/17 |
| 2020/0101221 A1* | 4/2020 | Lintereur ............. A61B 5/7275 |
| 2020/0101224 A1* | 4/2020 | Lintereur ............. G16H 40/40 |
| 2020/0135311 A1* | 4/2020 | Mairs ..................... G16H 10/60 |
| 2020/0246543 A1* | 8/2020 | Sadeghzadeh ....... A61B 5/7435 |
| 2020/0282141 A1* | 9/2020 | Rousson ................ G16H 20/17 |
| 2020/0342974 A1* | 10/2020 | Chen ................... A61M 5/1723 |
| 2021/0100486 A1* | 4/2021 | Romero Ugalde .... A61B 5/024 |
| 2022/0031946 A1 | 2/2022 | Parikh et al. |
| 2022/0044785 A1 | 2/2022 | Grosman et al. |

FOREIGN PATENT DOCUMENTS

| | | |
|---|---|---|
| CN | 104520862 A | 4/2015 |
| CN | 104756116 A | 7/2015 |
| CN | 104769595 A | 7/2015 |
| CN | 112005310 A | 11/2020 |
| CN | 113646847 A | 11/2021 |
| EP | 3785276 A1 | 3/2021 |
| EP | 3935646 A1 | 1/2022 |
| JP | 2003079723 A | 3/2003 |
| JP | 2005508025 A | 3/2005 |
| JP | 2008545493 A | 12/2008 |
| JP | 2010523167 A | 7/2010 |
| JP | 2010532044 A | 9/2010 |
| JP | 2011523940 A | 8/2011 |
| JP | 2021522582 A | 8/2021 |
| KR | 20210004993 A | 1/2021 |
| WO | 2014035570 A2 | 3/2014 |
| WO | 2014035672 A2 | 3/2014 |
| WO | WO-2016133879 A1 * | 8/2016 ......... A61B 5/14532 |
| WO | 2018033513 A1 | 2/2018 |
| WO | 2019209602 A1 | 10/2019 |
| WO | 2020214780 A1 | 10/2020 |

OTHER PUBLICATIONS

Kirchsteiger et al., Reduced hypoglycemia risk in insulin bolus therapy using asymmetric cost functions, Proceedings of the 7th Asian Control Conference, Hong Kong, China, Aug. 27-29, 2009 (Year: 2009).*

Colleen Suzanne Hughes, Safety Supervision System Design and Implications for Continuous Subcutaneous Insulin Infusion (CSII) in TIDM, Ph.D. dissertation, University of Virginia, Aug. 2011, 240 pgs (Year: 2011).*

Zarkogianni, et al., An Insulin Infusion Advisory System Based on Autotuning Nonlinear Model-Predictive Control, IEEE Transactions on Biomedical Engineering, vol. 58, No. 9, Sep. 2011, 11 pages (Year: 2011).*

Lee, Joon Bok, Thesis: Personalization and Enhanced Designs for Automated Glucose Control in Artificial Pancreas, University of California Santa Barbara, 152 pages, 2016 (Year: 2016).*

Zavitsanou et al., Embedded Control in Wearable Medical Devices: Application to the Artificial Pancreas, Processes 2016, 4, 35, 29 pages, 2016 (Year: 2016).*

Benyamin Grosman, et al., Personalized Closed Loop Medication Delivery System That Utilizes a Digital Twin of the Patient, Apr. 16, 2019, U.S. Appl. No. 16/386,104.

International Preliminary Report on Patentability dated Oct. 28, 2021, in PCT Application No. PCT/US2020/028461.

International Search Report and Written Opinion dated Jul. 9, 2020, in Application No. PCT/US2020/028461.

U.S. Non-Final Office Action dated Jan. 21, 2021, in U.S. Appl. No. 15/960,495.

U.S. Non-Final Office Action dated Mar. 31, 2021, in U.S. Appl. No. 16/386,104.

U.S. Notice of Allowance dated Jul. 20, 2021 in U.S. Appl. No. 16/386,104.

U.S. Notice of Allowance dated Jun. 29, 2021 in U.S. Appl. No. 15/960,495.

CN Office Action dated Oct. 12, 2023 in CN Application No. CN201980025847.6 with English translation.

JP Office Action dated Mar. 14, 2023 in Application No. JP2020-559417 with English translation.

U.S. Non-Final Office Action dated Oct. 6, 2023, in U.S. Appl. No. 17/504,568.

U.S. Non-Final Office Action dated Oct. 6, 2023, in U.S. Appl. No. 17/509,670.

* cited by examiner

PERSONALIZED CLOSED LOOP OPTIMIZATION SYSTEMS AND METHODS

TECHNICAL FIELD

Embodiments of the subject matter described herein relate generally to medical devices, and more particularly, embodiments of the subject matter relate to adjusting personalized settings of an infusion device for diabetes therapy management.

BACKGROUND

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source. Diabetes affects approximately eight percent of the total population in the United States alone.

Traditionally, because insulin cannot be taken orally, it has been injected with a syringe. Use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. Physicians have recognized that continuous infusion provides greater control of a diabetic's condition, and are also increasingly prescribing it for patients.

Patient-related and pump-related data can be collected during operation of an insulin infusion pump, for subsequent review and analysis. For example, glucose sensor data, insulin delivery data, and/or other data generated or collected by the infusion pump can be analyzed in an appropriate manner to determine whether or not it might be desirable to recommend changes to one or more settings of the infusion device. Accordingly, various settings of the infusion device can be adjusted in a patient-specific manner to improve and optimize the patient's therapy (in accordance with the analyzed data).

BRIEF SUMMARY

Medical devices and related systems and operating methods are provided. An embodiment of a method of automatically adjusting a control parameter for an operating mode of a medical device involves obtaining data pertaining to a physiological condition of a patient during operation of the medical device in accordance with the operating mode, determining a plurality of adjusted values for the control parameter based at least in part on the data, determining a respective cost associated with each respective adjusted value for the control parameter based at least in part on the data using a cost function, identifying, from among the plurality of adjusted values, an optimized value from among the plurality of adjusted values, wherein the optimized value has a minimum cost associated therewith from among the plurality of costs, and updating the control parameter at the medical device to the optimized value.

In another embodiment, a patient monitoring system is provided. The patient monitoring system includes a medical device to regulate a physiological condition of a patient in accordance with an operating mode based at least in part on a control parameter and a remote device to obtain patient data pertaining to operation of the medical device, determine a plurality of adjusted values for the control parameter based at least in part on the patient data, determine a respective cost associated with each respective adjusted value of the plurality of adjusted values for the control parameter based at least in part on the patient data using a cost function, resulting in a plurality of costs, identify an optimized value having a minimum cost associated therewith from among the plurality of adjusted values based on the plurality of costs, and update the control parameter to the optimized value, wherein subsequent operation of the medical device in accordance with the operating mode utilizes the optimized value for the control parameter.

In yet another embodiment, a method of automatically adjusting a control parameter for an operating mode of an infusion device regulating a glucose level of a patient is provided. The method involves obtaining patient data comprising sensed glucose measurement data and event log data during a period of operation of the infusion device in accordance with the operating mode and determining a plurality of adjusted values for the control parameter based at least in part on the sensed glucose measurement data. For each of the plurality of adjusted values for the control parameter, the method determines a simulated glucose profile for the patient corresponding to the period of operation based on the event log data and the respective adjusted value for the control parameter and determine a respective cost associated with the respective adjusted value for the control parameter based at least in part on the simulated glucose profile using an asymmetric cost function. The method continues by identifying, from among the plurality of adjusted values, an optimized value from among the plurality of adjusted values, wherein the optimized value has a minimum cost associated therewith from among a plurality of costs associated with the plurality of adjusted values according to the asymmetric cost function, and updating the control parameter at the infusion device to the optimized value, wherein subsequent operation of the infusion device utilizes the optimized value to generate dosage commands for delivering insulin to the patient.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
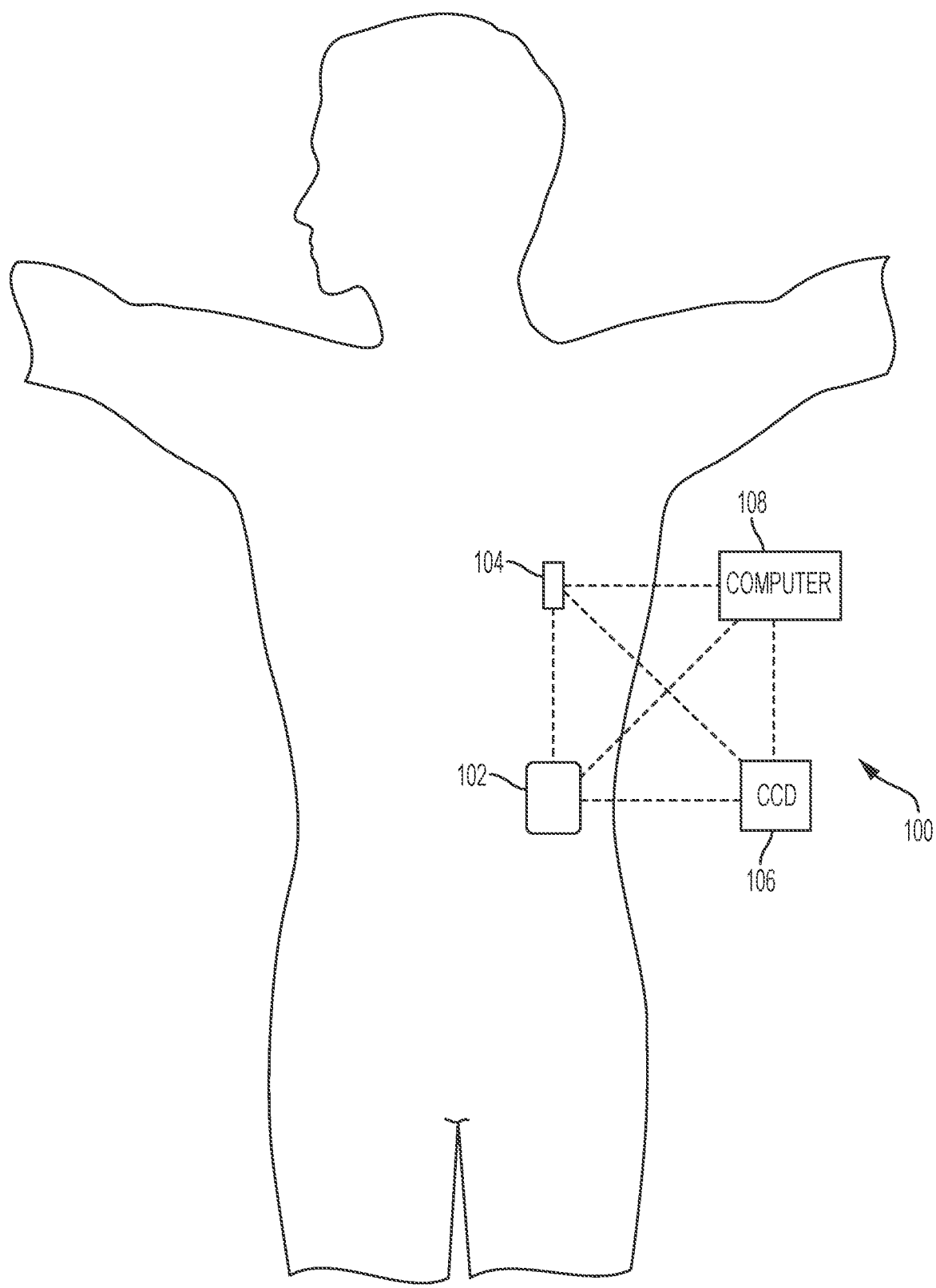
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to displace a plunger (or stopper) or other delivery mechanism to deliver a dosage of fluid, such as insulin, from a reservoir provided within the fluid infusion device to the body of a patient. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments of the subject matter described herein generally relate to automatically adjusting control parameters utilized by operating modes of an infusion device in a personalized manner based on updated patient data captured during preceding operation of the infusion device. For example, based on relationships between a patient's glucose measurement data during a preceding period of operation in a respective operating mode and a target glucose value or other reference or threshold values pertaining to that operating mode, a plurality of different adjusted values for one or more control parameters are identified, resulting in different sets of potential values for the control parameter(s) utilized by the respective operating mode. For each set of potential control parameter values, a corresponding simulated glucose profile is determined using the event log data (e.g., meal data, exercise data, sleep data, bolus data, and/or the like) corresponding to the preceding period of operation in the respective operating mode and the adjusted control parameter value(s). One or more cost functions are then applied to each of the simulated glucose profiles to determine a respective cost associated with each set of potential control parameter values, which, in turn is utilized to identify an optimized set of adjusted control parameter values that achieves the minimum cost. In this regard, exemplary embodiments may iteratively determine a cost associated with a set of potential control parameter values and iteratively determine an adjusted set of potential control parameter values using an optimization method until arriving at a minimum cost. Thereafter, the control parameter values for the operating mode are updated to reflect the optimized values, for example, by instructing or otherwise commanding the infusion device to overwrite or otherwise update the stored values for the control parameters of the operating mode maintained at the infusion device to reflect the optimized values. As described in greater detail below, in one or more exemplary embodiments, the cost function is asymmetric or otherwise disproportionately penalizes hypoglycemia or negative glucose excursions exhibited by the simulated glucose profiles to arrive at optimized personalized control parameter adjustments that mitigate the risk of hypoglycemia.

For purposes of explanation, the subject matter may be described herein in the context of a diabetes patient management system that generates and delivers recommendations for adjusting certain settings of an insulin infusion device used by a patient using a cloud-based architecture, wherein most of the processor-intensive tasks are performed by one or more server systems that communicate with other devices in the system, e.g., a mobile client device, a portable insulin infusion device, a source of data (such as patient-related data, insulin pump data, and the like), and possibly other remote devices. Patient-specific data collected during operation of the patient's insulin infusion device in an automated closed-loop mode is analyzed to determine recommended adjustments to certain settings of the insulin infusion device, which, in turn, may be subsequently applied during operation of the insulin infusion device in a manual delivery mode.

Infusion System Overview

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
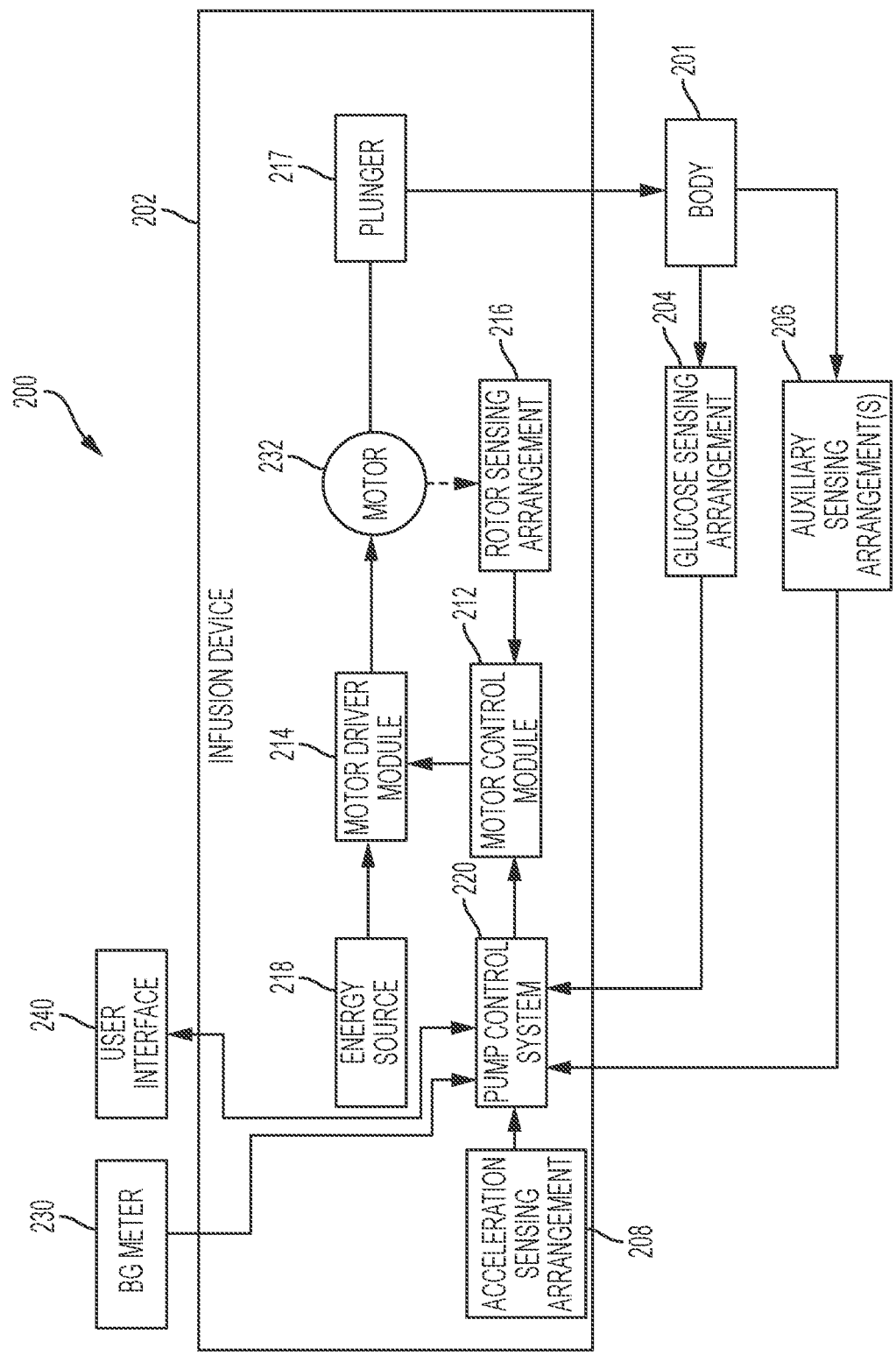
FIG. 2 is a block diagram of an exemplary control system suitable for use with a fluid infusion device in one or more embodiments.

FIG. 2 depicts an exemplary embodiment of a control system 200 suitable for use with an infusion device 202, such as the infusion device 102 described above. The control system 200 is capable of controlling or otherwise regulating a physiological condition in the body 201 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 204 (e.g., sensing arrangement 104) communicatively coupled to the infusion device 202. However, it should be noted that in alternative embodiments, the condition being regulated by the control system 200 may be correlative to the measured values obtained by the sensing arrangement 204. That said, for clarity and purposes of explanation, the subject matter may be described herein in the context of the sensing arrangement 204 being realized as a glucose sensing arrangement that senses, detects, measures or otherwise quantifies the patient's glucose level, which is being regulated in the body 201 of the patient by the control system 200.

In exemplary embodiments, the sensing arrangement 204 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 201 of the patient. The output electrical signals are filtered or otherwise processed to obtain a measurement value indicative of the patient's interstitial fluid glucose level. In exemplary embodiments, a blood glucose meter 230, such as a finger stick device, is utilized to directly sense, detect, measure or otherwise quantify the blood glucose in the body 201 of the patient. In this regard, the blood glucose meter 230 outputs or otherwise provides a measured blood glucose value that may be utilized as a reference measurement for calibrating the sensing arrangement 204 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 204 may alternatively be referred to herein as the sensor glucose value, the sensed glucose value, or variants thereof.

In the illustrated embodiment, the control system 200 also includes one or more additional sensing arrangements 206, 208 configured to sense, detect, measure or otherwise quantify a characteristic of the body 201 of the patient that is indicative of a condition in the body 201 of the patient. In this regard, in addition to the glucose sensing arrangement 204, one or more auxiliary sensing arrangements 206 may be worn, carried, or otherwise associated with the body 201 of the patient to measure characteristics or conditions of the patient (or the patient's activity) that may influence the patient's glucose levels or insulin sensitivity. For example, a heart rate sensing arrangement 206 could be worn on or otherwise associated with the patient's body 201 to sense, detect, measure or otherwise quantify the patient's heart rate, which, in turn, may be indicative of exercise (and the intensity thereof) that is likely to influence the patient's glucose levels or insulin response in the body 201. In yet another embodiment, another invasive, interstitial, or subcutaneous sensing arrangement 206 may be inserted into the body 201 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 206 could be realized as a standalone component worn by the patient, or alternatively, the auxiliary sensing arrangement(s) 206 may be integrated with the infusion device 202 or the glucose sensing arrangement 204.

The illustrated control system 200 also includes an acceleration sensing arrangement 208 (or accelerometer) that may be worn on or otherwise associated with the patient's body 201 to sense, detect, measure or otherwise quantify an acceleration of the patient's body 201, which, in turn, may be indicative of exercise or some other condition in the body 201 that is likely to influence the patient's insulin response. While the acceleration sensing arrangement 208 is depicted as being integrated into the infusion device 202 in FIG. 2, in alternative embodiments, the acceleration sensing arrangement 208 may be integrated with another sensing arrangement 204, 206 on the body 201 of the patient, or the acceleration sensing arrangement 208 may be realized as a separate standalone component that is worn by the patient.

In the illustrated embodiment, the pump control system 220 generally represents the electronics and other components of the infusion device 202 that control operation of the fluid infusion device 202 according to a desired infusion delivery program in a manner that is influenced by the sensed glucose value indicating the current glucose level in the body 201 of the patient. For example, to support a closed-loop operating mode, the pump control system 220 maintains, receives, or otherwise obtains a target or commanded glucose value, and automatically generates or otherwise determines dosage commands for operating an actuation arrangement, such as a motor 232, to displace the plunger 217 and deliver insulin to the body 201 of the patient based on the difference between the sensed glucose value and the target glucose value. In other operating modes, the pump control system 220 may generate or otherwise determine dosage commands configured to maintain the sensed glucose value below an upper glucose limit, above a lower glucose limit, or otherwise within a desired range of glucose values. In practice, the infusion device 202 may store or otherwise maintain the target value, upper and/or lower glucose limit(s), insulin delivery limit(s), and/or other glucose threshold value(s) in a data storage element accessible to the pump control system 220. As described in greater detail, in one or more exemplary embodiments, the pump control system 220 automatically adjusts or adapts one or more parameters or other control information used to generate commands for operating the motor 232 in a manner that accounts for a likely change in the patient's glucose level or insulin response resulting from a meal, exercise, or other activity.

Still referring to FIG. 2, the target glucose value and other threshold glucose values utilized by the pump control system 220 may be received from an external component (e.g., CCD 106 and/or computing device 108) or be input by a patient via a user interface element 240 associated with the infusion device 202. In practice, the one or more user interface element(s) 240 associated with the infusion device 202 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 240 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 2 depicts the user interface element(s) 240 as being separate from the infusion device 202, in practice, one or more of the user interface element(s) 240 may be integrated with the infusion device 202. Furthermore, in some embodiments, one or more user interface element(s) 240 are integrated with the sensing arrangement 204 in addition to and/or in alternative to the user interface element(s) 240 integrated with the infusion device 202. The user interface element(s) 240 may be manipulated by the patient to operate the infusion device 202 to deliver correction boluses, adjust target and/or threshold values, modify the delivery control scheme or operating mode, and the like, as desired.

Still referring to FIG. 2, in the illustrated embodiment, the infusion device 202 includes a motor control module 212 coupled to a motor 232 that is operable to displace a plunger 217 in a reservoir and provide a desired amount of fluid to the body 201 of a patient. In this regard, displacement of the plunger 217 results in the delivery of a fluid, such as insulin, that is capable of influencing the patient's physiological condition to the body 201 of the patient via a fluid delivery path (e.g., via tubing of an infusion set). A motor driver module 214 is coupled between an energy source 218 and the motor 232. The motor control module 212 is coupled to the motor driver module 214, and the motor control module 212 generates or otherwise provides command signals that operate the motor driver module 214 to provide current (or power) from the energy source 218 to the motor 232 to displace the plunger 217 in response to receiving, from a pump control system 220, a dosage command indicative of the desired amount of fluid to be delivered.

In exemplary embodiments, the energy source 218 is realized as a battery housed within the infusion device 202 that provides direct current (DC) power. In this regard, the motor driver module 214 generally represents the combination of circuitry, hardware and/or other electrical components configured to convert or otherwise transfer DC power provided by the energy source 218 into alternating electrical signals applied to respective phases of the stator windings of the motor 232 that result in current flowing through the stator windings that generates a stator magnetic field and causes the rotor of the motor 232 to rotate. The motor control module 212 is configured to receive or otherwise obtain a commanded dosage from the pump control system 220, convert the commanded dosage to a commanded translational displacement of the plunger 217, and command, signal, or otherwise operate the motor driver module 214 to cause the rotor of the motor 232 to rotate by an amount that produces the commanded translational displacement of the plunger 217. For example, the motor control module 212 may determine an amount of rotation of the rotor required to produce translational displacement of the plunger 217 that achieves the commanded dosage received from the pump control system 220. Based on the current rotational position (or orientation) of the rotor with respect to the stator that is indicated by the output of the rotor sensing arrangement 216, the motor control module 212 determines the appropriate sequence of alternating electrical signals to be applied to the respective phases of the stator windings that should rotate the rotor by the determined amount of rotation from its current position (or orientation). In embodiments where the motor 232 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 212 operates the motor driver module 214 to apply the determined alternating electrical signals (e.g., the command signals) to the stator windings of the motor 232 to achieve the desired delivery of fluid to the patient.

When the motor control module 212 is operating the motor driver module 214, current flows from the energy source 218 through the stator windings of the motor 232 to produce a stator magnetic field that interacts with the rotor magnetic field. In some embodiments, after the motor control module 212 operates the motor driver module 214 and/or motor 232 to achieve the commanded dosage, the motor control module 212 ceases operating the motor driver module 214 and/or motor 232 until a subsequent dosage command is received. In this regard, the motor driver module 214 and the motor 232 enter an idle state during which the motor driver module 214 effectively disconnects or isolates the stator windings of the motor 232 from the energy source 218. In other words, current does not flow from the energy source 218 through the stator windings of the motor 232 when the motor 232 is idle, and thus, the motor 232 does not consume power from the energy source 218 in the idle state, thereby improving efficiency.

Depending on the embodiment, the motor control module 212 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 212. The computer-executable programming instructions, when read and executed by the motor control module 212, cause the motor control module 212 to perform or otherwise support the tasks, operations, functions, and processes described herein.

It should be appreciated that FIG. 2 is a simplified representation of the infusion device 202 for purposes of explanation and is not intended to limit the subject matter described herein in any way. In this regard, depending on the embodiment, some features and/or functionality of the sensing arrangement 204 may implemented by or otherwise integrated into the pump control system 220, or vice versa. Similarly, in practice, the features and/or functionality of the motor control module 212 may implemented by or otherwise integrated into the pump control system 220, or vice versa. Furthermore, the features and/or functionality of the pump control system 220 may be implemented by control electronics located in the fluid infusion device 202, while in alternative embodiments, the pump control system 220 may be implemented by a remote computing device that is physically distinct and/or separate from the infusion device 202, such as, for example, the CCD 106 or the computing device 108.

Figure 3:
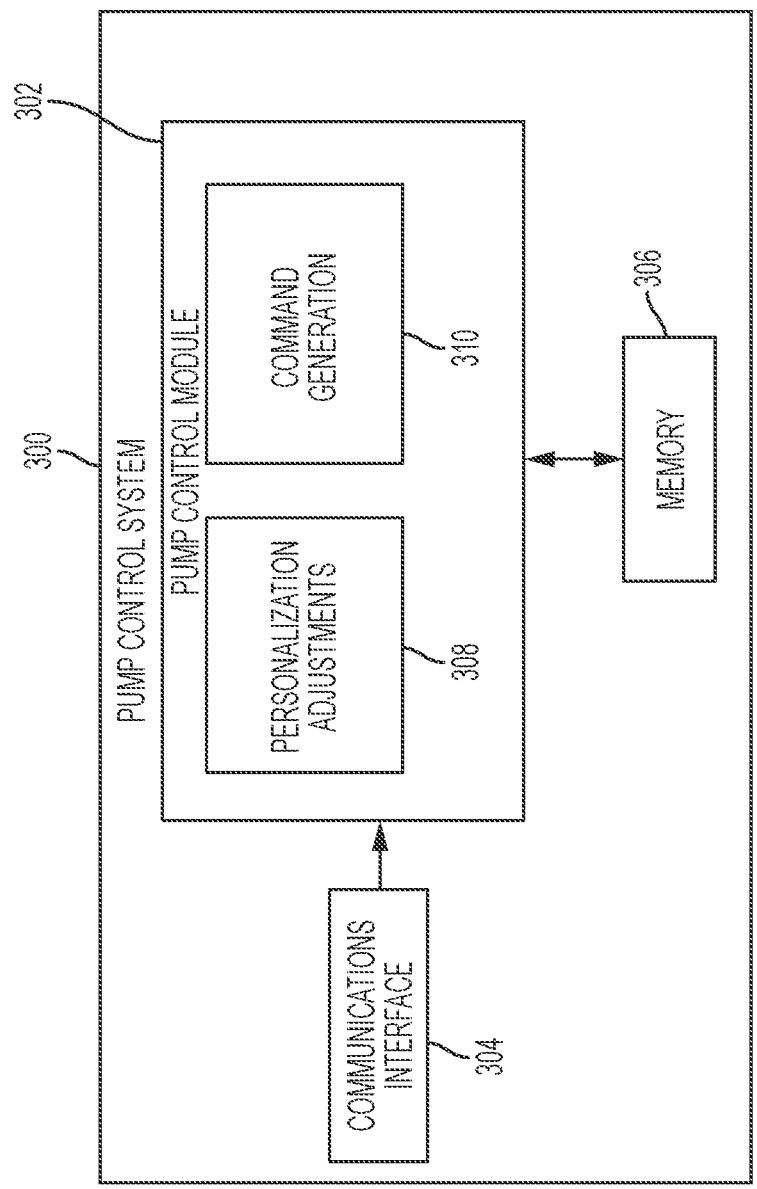
FIG. 3 is a block diagram of an exemplary pump control system suitable for use in the infusion device in the control system of FIG. 2 in one or more embodiments.

FIG. 3 depicts an exemplary embodiment of a pump control system 300 suitable for use as the pump control system 220 in FIG. 2 in accordance with one or more embodiments. The illustrated pump control system 300 includes, without limitation, a pump control module 302, a communications interface 304, and a data storage element (or memory) 306. The pump control module 302 is coupled to the communications interface 304 and the memory 306, and the pump control module 302 is suitably configured to support the operations, tasks, and/or processes described herein. In various embodiments, the pump control module 302 is also coupled to one or more user interface elements (e.g., user interface 240) for receiving user inputs (e.g., target glucose values or other glucose thresholds) and providing notifications, alerts, or other therapy information to the patient.

The communications interface 304 generally represents the hardware, circuitry, logic, firmware and/or other components of the pump control system 300 that are coupled to the pump control module 302 and configured to support communications between the pump control system 300 and the various sensing arrangements 204, 206, 208. In this regard, the communications interface 304 may include or otherwise be coupled to one or more transceiver modules capable of supporting wireless communications between the pump control system 220, 300 and the sensing arrangement(s) 204, 206, 208. For example, the communications interface 304 may be utilized to receive sensor measurement values or other measurement data from each sensing arrangement 204, 206, 208 in a control system 200. In other embodiments, the communications interface 304 may be configured to support wired communications to/from the sensing arrangement(s) 204, 206, 208. In various embodiments, the communications interface 304 may also support communications with another electronic device (e.g., CCD 106 and/or computer 108) in an infusion system (e.g., to upload sensor measurement values to a server or other computing device, receive control information from a server or other computing device, and the like).

The pump control module 302 generally represents the hardware, circuitry, logic, firmware and/or other component of the pump control system 300 that is coupled to the communications interface 304 and configured to determine dosage commands for operating the motor 232 to deliver fluid to the body 201 based on measurement data received from the sensing arrangements 204, 206, 208 and perform various additional tasks, operations, functions and/or operations described herein. For example, in exemplary embodiments, pump control module 302 implements or otherwise executes a command generation application 310 that supports one or more autonomous operating modes and calculates or otherwise determines dosage commands for operating the motor 232 of the infusion device 202 in an autonomous operating mode based at least in part on a current measurement value for a condition in the body 201 of the patient. For example, in a closed-loop operating mode, the command generation application 310 may determine a dosage command for operating the motor 232 to deliver insulin to the body 201 of the patient based at least in part on the current glucose measurement value most recently received from the sensing arrangement 204 to regulate the patient's blood glucose level to a target reference glucose value. Additionally, the command generation application 310 may generate dosage commands for boluses that are manually-initiated or otherwise instructed by a patient via a user interface element.

In exemplary embodiments, the pump control module 302 also implements or otherwise executes a personalization application 308 that is cooperatively configured to interact with the command generation application 310 to support adjusting dosage commands or control information dictating the manner in which dosage commands are generated in a personalized, patient-specific manner. In this regard, in some embodiments, based on correlations between current and recent measurement data and the current operational context relative to historical data associated with the patient, the personalization application 308 may adjust or otherwise modify values for one or more parameters utilized by the command generation application 310 when determining dosage commands, for example, by modifying a parameter value at a register or location in memory 306 referenced by the command generation application 310. In yet other embodiments, the personalization application 308 may predict meals or other events or activities that are likely to be engaged in by the patient and output or otherwise provide an indication of the predicted patient behavior, which, in turn, may then be utilized to adjust the manner in which dosage commands are generated to regulate glucose in a manner that accounts for the patient's predicted behavior in a personalized manner. In some embodiments, the personalization application 308 may support automatically performing personalized adjustments of control parameters utilized by the command generation application 310.

Still referring to FIG. 3, depending on the embodiment, the pump control module 302 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 302, or in any practical combination thereof. In exemplary embodiments, the pump control module 302 includes or otherwise accesses the data storage element or memory 306, which may be realized using any sort of non-transitory computer-readable medium capable of storing programming instructions for execution by the pump control module 302. The computer-executable programming instructions, when read and executed by the pump control module 302, cause the pump control module 302 to implement or otherwise generate the applications 308, 310 and perform tasks, operations, functions, and processes described herein.

It should be understood that FIG. 3 is a simplified representation of a pump control system 300 for purposes of explanation and is not intended to limit the subject matter described herein in any way. For example, in some embodiments, the features and/or functionality of the motor control module 212 may be implemented by or otherwise integrated into the pump control system 300 and/or the pump control module 302, for example, by the command generation application 310 converting the dosage command into a corresponding motor command, in which case, the separate motor control module 212 may be absent from an embodiment of the infusion device 202.

Figure 4:
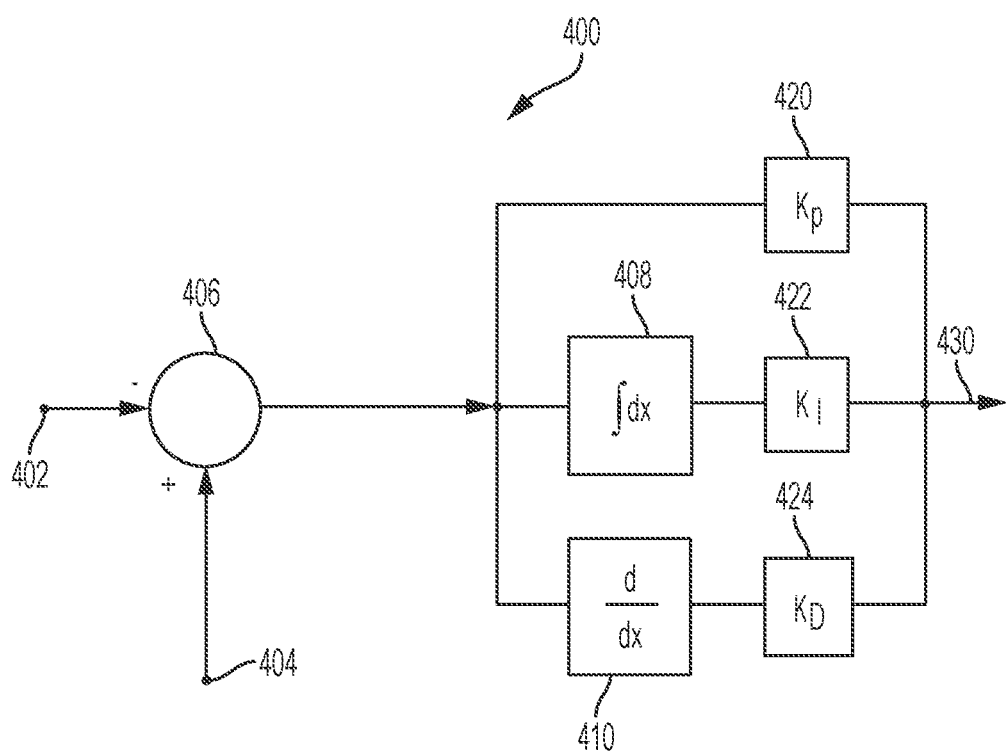
FIG. 4 is a block diagram of a closed-loop control system that may be implemented or otherwise supported by the pump control system in the fluid infusion device of FIGS. 2-3 in one or more exemplary embodiments.

FIG. 4 depicts an exemplary closed-loop control system 400 that may be implemented by a pump control system 220, 300 to provide a closed-loop operating mode that autonomously regulates a condition in the body of a patient to a reference (or target) value. It should be appreciated that FIG. 4 is a simplified representation of the control system 400 for purposes of explanation and is not intended to limit the subject matter described herein in any way.

In exemplary embodiments, the control system 400 receives or otherwise obtains a target glucose value at input 402. In some embodiments, the target glucose value may be stored or otherwise maintained by the infusion device 202 (e.g., in memory 306), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 400 also receives or otherwise obtains a current glucose measurement value (e.g., the most recently obtained sensor glucose value) from the sensing arrangement 204 at input 404. The illustrated control system 400 implements or otherwise provides proportional-integral-derivative (PID) control to determine or otherwise generate delivery commands for operating the motor 232 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 402 and the measured glucose level at input 404 to generate or otherwise determine a dosage (or delivery) command provided at output 430. Based on that delivery command, the motor control module 212 operates the motor 232 to deliver insulin to the body of the patient to influence the patient's glucose level, and thereby reduce the difference between a subsequently measured glucose level and the target glucose level.

The illustrated control system 400 includes or otherwise implements a summation block 406 configured to determine a difference between the target value obtained at input 402 and the measured value obtained from the sensing arrangement 204 at input 404, for example, by subtracting the target value from the measured value. The output of the summation block 406 represents the difference between the measured and target values, which is then provided to each of a proportional term path, an integral term path, and a derivative term path. The proportional term path includes a gain block 420 that multiplies the difference by a proportional gain coefficient, $K_P$, to obtain the proportional term. The integral term path includes an integration block 408 that integrates the difference and a gain block 422 that multiplies the integrated difference by an integral gain coefficient, $K_I$, to obtain the integral term. The derivative term path includes a derivative block 410 that determines the derivative of the difference and a gain block 424 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 430. Various implementation details pertaining to closed-loop PID control and determining gain coefficients are described in greater detail in U.S. Pat. No. 7,402,153, which is incorporated by reference.

In one or more exemplary embodiments, the PID gain coefficients are patient-specific and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 202. The PID gain coefficients may be maintained by the memory 306 accessible to the pump control module 302. In this regard, the memory 306 may include a plurality of registers associated with the control parameters for the PID control. For example, a first parameter register may store the target glucose value and be accessed by or otherwise coupled to the summation block 406 at input 402, and similarly, a second parameter register accessed by the proportional gain block 420 may store the proportional gain coefficient, a third parameter register accessed by the integration gain block 422 may store the integration gain coefficient, and a fourth parameter register accessed by the derivative gain block 424 may store the derivative gain coefficient.

Figure 5:
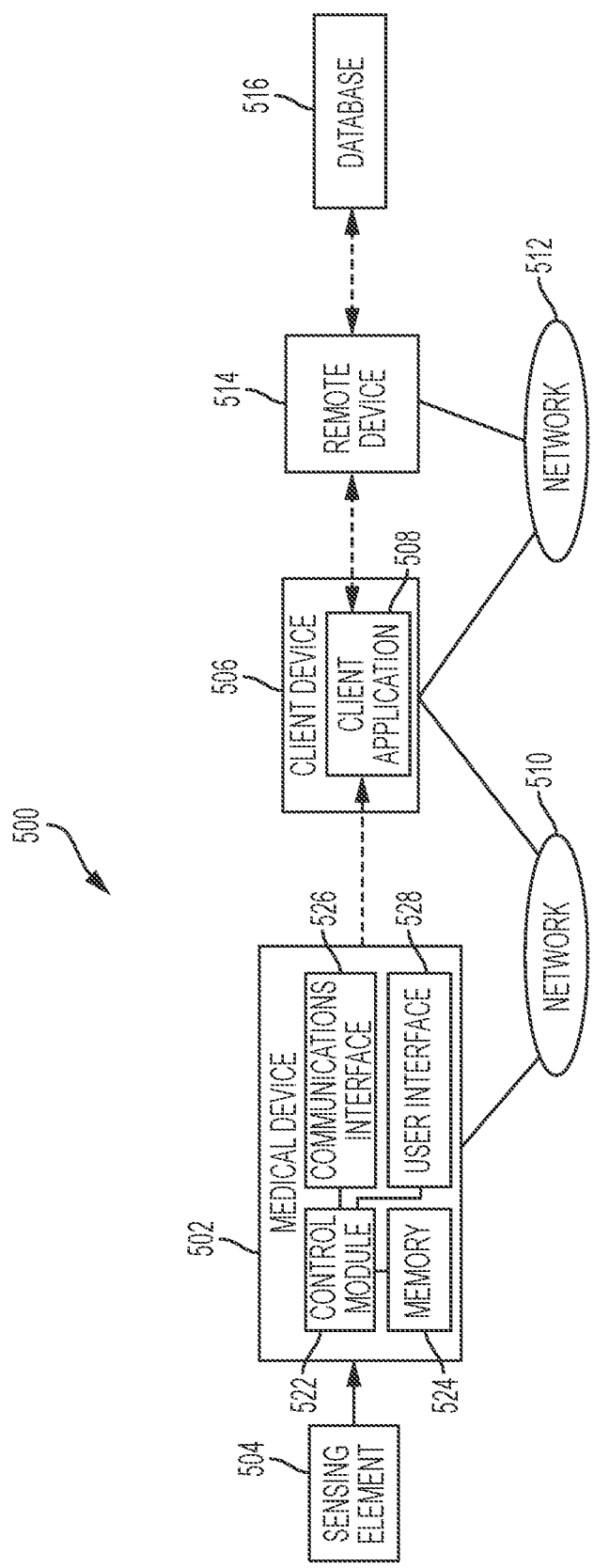
FIG. 5 is a block diagram of an exemplary patient monitoring system.

FIG. 5 depicts an exemplary embodiment of a patient monitoring system 500. The patient monitoring system 500 includes a medical device 502 that is communicatively coupled to a sensing element 504 that is inserted into the body of a patient or otherwise worn by the patient to obtain measurement data indicative of a physiological condition in the body of the patient, such as a sensed glucose level. The medical device 502 is communicatively coupled to a client device 506 via a communications network 510, with the client device 506 being communicatively coupled to a remote device 514 via another communications network 512. In this regard, the client device 506 may function as an intermediary for uploading or otherwise providing measurement data from the medical device 502 to the remote device 514. It should be appreciated that FIG. 5 depicts a simplified representation of a patient monitoring system 500 for purposes of explanation and is not intended to limit the subject matter described herein in any way.

In exemplary embodiments, the client device 506 is realized as a mobile phone, a smartphone, a tablet computer, or other similar mobile electronic device; however, in other embodiments, the client device 506 may be realized as any sort of electronic device capable of communicating with the medical device 502 via network 510, such as a laptop or notebook computer, a desktop computer, or the like. In exemplary embodiments, the network 510 is realized as a Bluetooth network, a ZigBee network, or another suitable personal area network. That said, in other embodiments, the network 510 could be realized as a wireless ad hoc network, a wireless local area network (WLAN), or local area network (LAN). The client device 506 includes or is coupled to a display device, such as a monitor, screen, or another conventional electronic display, capable of graphically presenting data and/or information pertaining to the physiological condition of the patient. The client device 506 also includes or is otherwise associated with a user input device, such as a keyboard, a mouse, a touchscreen, or the like, capable of receiving input data and/or other information from the user of the client device 506.

In some embodiments, a user, such as the patient, the patient's doctor or another healthcare provider, or the like, manipulates the client device 506 to execute a client application 508 that supports communicating with the medical device 502 via the network 510. In this regard, the client application 508 supports establishing a communications session with the medical device 502 on the network 510 and receiving data and/or information from the medical device 502 via the communications session. The medical device 502 may similarly execute or otherwise implement a corresponding application or process that supports establishing the communications session with the client application 508. The client application 508 generally represents a software module or another feature that is generated or otherwise implemented by the client device 506 to support the processes described herein. Accordingly, the client device 506 generally includes a processing system and a data storage element (or memory) capable of storing programming instructions for execution by the processing system, that, when read and executed, cause processing system to create, generate, or otherwise facilitate the client application 508 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 506 and the medical device 502 establish an association (or pairing) with one another over the network 510 to support subsequently establishing a point-to-point communications session between the medical device 502 and the client device 506 via the network 510. For example, in accordance with one embodiment, the network 510 is realized as a Bluetooth network, wherein the medical device 502 and the client device 506 are paired with one another (e.g., by obtaining and storing network identification information for one another) by performing a discovery procedure or another suitable pairing procedure. The pairing information obtained during the discovery procedure allows either of the medical device 502 or the client device 506 to initiate the establishment of a secure communications session via the network 510.

In one or more exemplary embodiments, the client application 508 is also configured to store or otherwise maintain an address and/or other identification information for the remote device 514 on the second network 512. In this regard, the second network 512 may be physically and/or logically distinct from the network 510, such as, for example, the Internet, a cellular network, a wide area network (WAN), or the like. The remote device 514 generally represents a server or other computing device configured to receive and analyze or otherwise monitor measurement data, event log data, and potentially other information obtained for the patient associated with the medical device 502. In exemplary embodiments, the remote device 514 is coupled to a database 516 configured to store or otherwise maintain data associated with individual patients. In practice, the remote device 514 may reside at a location that is physically distinct and/or separate from the medical device 502 and the client device 506, such as, for example, at a facility that is owned and/or operated by or otherwise affiliated with a manufacturer of the medical device 502. For purposes of explanation, but without limitation, the remote device 514 may alternatively be referred to herein as a server.

It should be noted that in some embodiments, some or all of the functionality and processing intelligence of the remote computing device 514 can reside at the medical device 502 and/or at other components or computing devices that are compatible with the patient monitoring system 500. In other words, the patient monitoring system 500 need not rely on a network-based or a cloud-based server arrangement as depicted in FIG. 5, although such a deployment might be the most efficient and economical implementation. These and other alternative arrangements are contemplated by this disclosure. To this end, some embodiments of the system 500 may include additional devices and components that serve as data sources, data processing units, and/or recommendation delivery mechanisms. For example, the system 500 may include any or all of the following elements, without limitation: computer devices or systems; patient monitors; healthcare provider systems; data communication devices; and the like.

Still referring to FIG. 5, the sensing element 504 generally represents the component of the patient monitoring system 500 that is configured to generate, produce, or otherwise output one or more electrical signals indicative of a physiological condition that is sensed, measured, or otherwise quantified by the sensing element 504. In this regard, the physiological condition of a patient influences a characteristic of the electrical signal output by the sensing element 504, such that the characteristic of the output signal corresponds to or is otherwise correlative to the physiological condition that the sensing element 504 is sensitive to. In exemplary embodiments, the sensing element 504 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 504.

The medical device 502 generally represents the component of the patient monitoring system 500 that is communicatively coupled to the output of the sensing element 504 to receive or otherwise obtain the measurement data samples from the sensing element 504 (e.g., the measured glucose and characteristic impedance values), store or otherwise maintain the measurement data samples, and upload or otherwise transmit the measurement data to the server 514 via the client device 506. In one or more embodiments, the medical device 502 is realized as an infusion device 102, 202 configured to deliver a fluid, such as insulin, to the body of the patient. That said, in other embodiments, the medical device 502 could be a standalone sensing or monitoring device separate and independent from an infusion device (e.g., sensing arrangement 104, 204), such as, for example, a continuous glucose monitor (CGM), an interstitial glucose sensing arrangement, or similar device. It should be noted that although FIG. 5 depicts the medical device 502 and the sensing element 504 as separate components, in practice, the medical device 502 and the sensing element 504 may be integrated or otherwise combined to provide a unitary device that can be worn by the patient.

In exemplary embodiments, the medical device 502 includes a control module 522, a data storage element 524 (or memory), a communications interface 526, and a user interface 528. The user interface 528 generally represents the input user interface element(s) and/or output user interface element(s) associated with the medical device 502 (e.g., one or more user interface elements 240). The control module 522 generally represents the hardware, circuitry, logic, firmware and/or other component(s) of the medical device 502 that is coupled to the sensing element 504 to receive the electrical signals output by the sensing element 504 and perform or otherwise support various additional tasks, operations, functions and/or processes described herein. Depending on the embodiment, the control module 522 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 522 includes an analog-to-digital converter (ADC) or another similar sampling arrangement that samples or otherwise converts an output electrical signal received from the sensing element 504 into corresponding digital measurement data value. In other embodiments, the sensing element 504 may incorporate an ADC and output a digital measurement value.

The communications interface 526 generally represents the hardware, circuitry, logic, firmware and/or other components of the medical device 502 that are coupled to the control module 522 for outputting data and/or information from/to the medical device 502 to/from the client device 506. For example, the communications interface 526 may include or otherwise be coupled to one or more transceiver modules capable of supporting wireless communications between the medical device 502 and the client device 506. In exemplary embodiments, the communications interface 526 is realized as a Bluetooth transceiver or adapter configured to support Bluetooth Low Energy (BLE) communications.

In exemplary embodiments, the remote device 514 receives, from the client device 506, measurement data values associated with a particular patient (e.g., sensor glucose measurements, acceleration measurements, and the like) that were obtained using the sensing element 504, and the remote device 514 stores or otherwise maintains the historical measurement data in the database 516 in association with the patient (e.g., using one or more unique patient identifiers). Additionally, the remote device 514 may also receive, from or via the client device 506, meal data or other event log data that may be input or otherwise provided by the patient (e.g., via client application 508) and store or otherwise maintain historical meal data and other historical event or activity data associated with the patient in the database 516. In this regard, the meal data include, for example, a time or timestamp associated with a particular meal event, a meal type or other information indicative of the content or nutritional characteristics of the meal, and an indication of the size associated with the meal. In exemplary embodiments, the remote device 514 also receives historical fluid delivery data corresponding to basal or bolus dosages of fluid delivered to the patient by an infusion device 102, 202. For example, the client application 508 may communicate with an infusion device 102, 202 to obtain insulin delivery dosage amounts and corresponding timestamps from the infusion device 102, 202, and then upload the insulin delivery data to the remote device 514 for storage in association with the particular patient. The remote device 514 may also receive geolocation data and potentially other contextual data associated with a device 502, 506 from the client device 506 and/or client application 508, and store or otherwise maintain the historical operational context data in association with the particular patient. In this regard, one or more of the devices 502, 506 may include a global positioning system (GPS) receiver or similar modules, components or circuitry capable of outputting or otherwise providing data characterizing the geographic location of the respective device 502, 506 in real-time.

The historical patient data may be analyzed by one or more of the remote device 514, the client device 506, and/or the medical device 502 to alter or adjust operation of an infusion device 102, 202 to influence fluid delivery in a personalized manner. In exemplary embodiments described herein, historical patient data is utilized to develop a pharmacokinetic/pharmacodynamic (PK/PD) model for individual patients supported by the patient monitoring system 500. For example, in one embodiment, for each individual patient, a "digital twin" that includes a patient-specific PK/PD model and a fixed profile of meal absorption rates as a function of time (as identified from the patient's historical data) is generated and utilized to personalize infusion device settings for that individual patient. In this context, a digital twin is a mathematical model or simulation of an individual patient that includes a set of differential equations derived from the patient's historical data that together define or describe the patient's blood glucose response to carbohydrate intake and insulin delivery. In this regard, the resulting patient-specific PK/PD model used for the digital twin represents the model that best fits the patient's historical sensor glucose measurement data for the period of time under evaluation used to generate the model. The "output" of the digital twin is a predicted blood glucose level or profile based on "inputs" that are likely to influence the patient's glycemic state, such as an amount of insulin delivered, an amount of carbohydrate consumed, and/or the like, in conjunction with the various patient-specific parameter values associated with the model. For example, each digital twin may be associated with a personalized and patient-specific set of values for various closed-loop control parameters (e.g., PID gain coefficient values, PID time constants, basal insulin delivery rates, carbohydrate ratios, insulin sensitivity factors, target glucose values, and the like), which may be unique to each individual patient.

Depending on the embodiment, the digital twin may be updated on a periodic basis (e.g., daily, weekly, or the like), at scheduled intervals, or in response to new or updated patient data being uploaded to the remote server 514 and/or database 516 (e.g., new or more recent sensor glucose measurement data samples, insulin delivery amounts, meal event log data, and the like). Additional details regarding the development of a digital twin are provided in U.S. patent application Ser. No. 16/386,104, filed Apr. 16, 2019, and incorporated by reference herein in its entirety. As described in greater detail below, in one or more exemplary embodiments, a cloud-based digital twin for an individual patient is managed and/or maintained by the remote server 514 and/or database 516 and utilized automatically configure and adjust settings, gains, and parameters for that patient's infusion device 502. That said, in alternative embodiments where the infusion device has sufficient processing capabilities, the creation, updating, and management of the digital twin may be implemented at the infusion device 502 in lieu of a cloud-based implementation.

Personalization Optimization

In exemplary embodiments, an infusion device is configured to support multiple operating modes where aspects of fluid delivery are automatically and/or autonomously controlled and governed using patient-specific parameter values that are stored or otherwise maintained at the infusion device. For example, a dual-mode insulin infusion device is capable of operating in a manual insulin delivery mode, in which the infusion device delivers basal insulin according to a pre-programmed rate or a time-based rate profile and/or other applicable manual mode settings, or in an automated closed-loop insulin delivery mode, in which the infusion device utilizes applicable closed-loop settings to influence the manner in which basal insulin delivery is automatically adjusted based on a relationship between a measured glucose value and a target glucose value (or set point), as described above. That said, it should be appreciated that the subject matter described herein is not limited to any particular type or number of operating modes supported by an infusion device.

As described in U.S. patent application Ser. No. 15/960, 495, which is incorporated by reference herein, after a period of operation in the closed-loop mode, the total daily basal insulin delivered tends to reach a more optimal level due to the constant adjustment of insulin delivery by the feedback controller. Thus, the efficacy of pre-programmed basal rates and other parameter values for various operating mode settings may wane over time due to a variety of reasons. Accordingly, in exemplary embodiments described herein, personalized infusion device settings are dynamically updated to achieve a better outcome for the patient in response to updated patient data collected or otherwise obtained during operation of the infusion device. In this regard, one or more cost functions may be utilized to arrive at patient-specific values for operating mode parameters that are likely to achieve a desired relationship between maximizing the amount of time the patient's glucose level is likely to be within a normal glycemic range (e.g., an euglycemic range), minimizing the deviations between the patient's glucose level and a target glucose level, and minimizing the likelihood, probability, or time spent in a hypoglycemic range.

Figure 6:
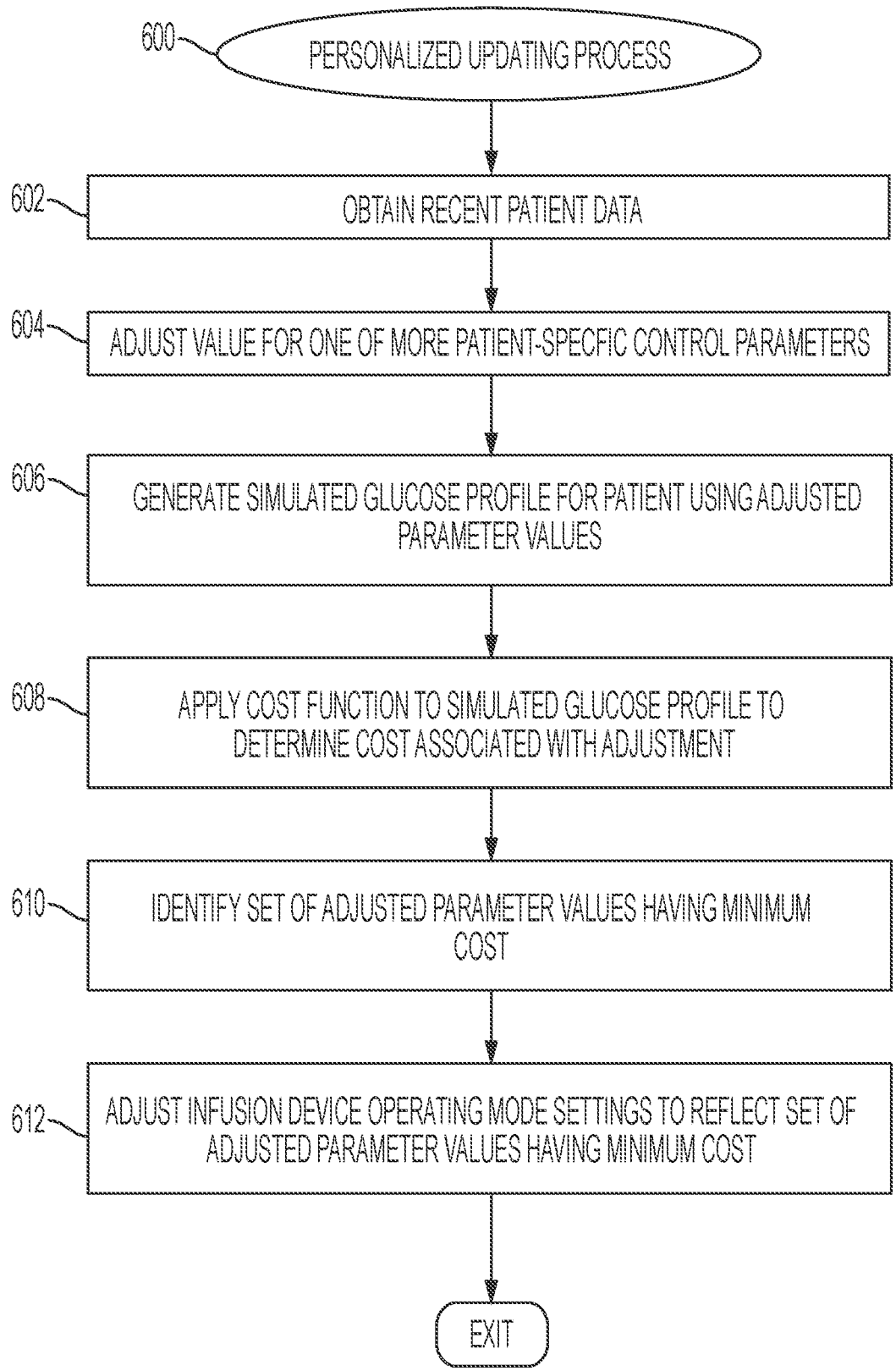
FIG. 6 is a flow diagram of an exemplary personalized updating process suitable for use with a medical device in one or more exemplary embodiments.

FIG. 6 depicts an exemplary personalized updating process 600 for dynamically updating operating mode control parameters with patient-specific values in real-time based on recent patient data to reflect changes to the patient's physiological characteristics in an ongoing manner. The various tasks performed in connection with the personalized updating process 600 may be performed by hardware, firmware, software executed by processing circuitry, or any combination thereof. For illustrative purposes, the following description refers to elements mentioned above in connection with FIGS. 1-5. For purposes of explanation, the personalized updating process 600 may be described herein primarily in the context of being implemented at a remote server 514 in a patient monitoring system 500. It should be appreciated that the personalized updating process 600 may include any number of additional or alternative tasks, the tasks need not be performed in the illustrated order and/or the tasks may be performed concurrently, and/or the personalized updating process 600 may be incorporated into a more comprehensive procedure or process having additional functionality not described in detail herein. Moreover, one or more of the tasks shown and described in the context of FIG. 6 could be omitted from a practical embodiment of the personalized updating process 600 as long as the intended overall functionality remains intact.

Depending on the embodiment, the personalized updating process 600 may be performed on a periodic basis (e.g., daily, weekly, etc.), at a scheduled time of day (e.g., during an overnight period), in response to a manually initiating an update to his or her infusion device, or in response to more recent or updated patient data being available (e.g., in response to a batch of more recent measurement and delivery data being uploaded from an infusion device to a remote server and/or database). The personalized updating process 600 receives or otherwise obtains patient data pertaining to recent operation of the patient's infusion device, adjusts or otherwise alters the values for one or more control parameters for purposes of simulating the patient's physiological response based on the obtained patient data, and generates a simulated glucose profile for the patient using the adjusted control parameter values and the recent patient data (tasks 602, 604, 606). For example, the patient's infusion device 502 and/or client device 506 may upload recent sensor glucose measurement data, insulin delivery data, event log data, and the like to the remote device 514 for purposes of updating an individual's historical patient data maintained in the database 516. Thereafter, the remote device 514 builds or otherwise creates a model associated with the patient that can be utilized to generate a simulated glucose profile for the patient based on the recent event log data (e.g., the recent meal data, exercise information, sleep information, and/or the like), and then adjusts one or more control parameter values based on the relationship between the simulated glucose profile and one or more target glucose values (e.g., the patient's target glucose or set point for the closed-loop mode, hypoglycemia and/or hyperglycemia thresholds, and/or the like). For example, in exemplary embodiments where a digital twin for the patient is maintained (e.g., in the database 516), the remote server 514 utilizes that patient's particular PK/PD model to generate predicted sensor glucose measurement values for the period of time after generation of the patient's digital twin based on the patient's meal data, exercise data, bolus data, sleep data, and the like during that time period that would result from simulated operation of the patient's infusion device 502 using the adjusted control parameter values.

After generating a simulated glucose profile for the patient, the personalized updating process 600 applies one or more cost functions to the simulated glucose profile to calculate or otherwise determine a total cost associated with utilizing the adjusted control parameter values (task 608). As described in greater detail below, in exemplary embodiments, the cost is influenced by the relationship between the simulate glucose values and a target glucose value, such that adjustments to the control parameter values that reduce the difference between the simulated glucose values and the target glucose value will have a lower cost associated therewith. After determining the cost associated with a given set of control parameter values, the illustrated personalized updating process 600 verifies or otherwise identifies whether that set of control parameter values achieves a minimum cost from among a number of potential sets of control parameter values (task 610). In this regard, the tasks of adjusting control parameter values (task 604), determining simulated glucose profiles (task 606), and determining the cost associated with a respective set of adjusted control parameter values (task 608) may be repeated or otherwise performed multiple times to obtain different potential sets of adjusted control parameter values and corresponding costs associated therewith. Any number of different multivariate parameter optimization methods may be utilized to identify a respective set of adjusted control parameter values that is likely or expected to reduce costs, with the tasks 604, 606, and 608 being iteratively repeated using an optimization method to adjust one or more control parameter values (task 604) and determine a corresponding glucose profile and cost (tasks 606 and 608), which, in turn may be utilized by the optimization method to iteratively adjust the control parameter value(s) until arriving at a minimum cost. Additionally, in some embodiments, a reference cost associated with the set of control parameter values corresponding to current infusion device settings may be determined based on the recent sensor glucose measurement data received by the remote device 514 and/or database 516. In such embodiments, if the set of control parameter values corresponding to current infusion device settings yield the minimum cost, the personalized updating process 600 may exit and maintain the current infusion device settings without making any adjustments to the infusion device settings.

After identifying the set of control parameter values that yields the minimum cost, personalized updating process 600 updates or otherwise adjusts the infusion device settings to reflect the adjusted control parameter values (task 612). For example, the remote server 514 may push or otherwise transmit a command or instruction to the infusion device 502 and/or client device 506 that indicates the adjusted patient-specific control parameter values to be implemented, which, in turn results in the stored values for those operating mode control parameters (e.g., at designated registers or locations in memory 306) being updated to the adjusted patient-specific control parameter values. Thereafter, the control system of the infusion device 502 (e.g., command generation application 310 or closed-loop control system 400) automatically references or otherwise utilizes the updated adjusted patient-specific control parameter values when generating dosage commands for operating the infusion device 502 to deliver fluid to the patient.

Still referring to FIG. 6, in general, the goal of insulin delivery therapy is to inject appropriate amount of insulin at various circumstances to regulate patient's glucose level to maximize the time spent in a normal range, for example from 80 mg/dL to 150 mg/dL. Additionally, or alternatively, the effectiveness of therapy can be evaluated by a mathematical cost function that calculates a cost based on how much a patient's glucose profile deviates from a control target or other reference value (e.g., the midpoint of the normal glycemic range). For example, the cost associated with a glucose profile deviating from a target can be determined using a first equation (alternatively referred to herein as equation 1):

$$f = \frac{\sum_{k=1}^{n} |BG_k - TG|}{n},$$

where $BG_k$ represents an individual blood glucose sample of the glucose profile, TG represents the reference or target glucose value, n represents the total number blood glucose samples under consideration, and $f$ is the total cost associated with the glucose profile. Alternatively, the cost can be determined using the equation (equation 2):

$$f = \frac{\sum_{k=1}^{n} (BG_k - TG)^2}{n}.$$

In some embodiments, the cost function can be normalized using a normalization factor, p, using the equation (equation 3):

$$f = \frac{\sum_{k=1}^{n} \left(\frac{BG_k - TG}{p}\right)^2}{n}.$$

The normalization factor (p) can be utilized to normalize the cost to a value between 0 and 1, which can increase accuracy and reduce the number of iterations required to converge on an optimum or minimum cost. In this regard, in some embodiments, the normalization factor (p) may vary based on the glucose level ($BG_k$). For example, if the difference between the glucose profile and the target glucose value ($BG_k$-TG) is never greater than 100, then the normalization factor can be set to the value of 100 (p=100). In this regard, in some embodiments, p may be set to the maximum difference between the glucose profile and the target glucose value.

The foregoing cost functions are symmetric, in that they proportionally assign cost for both positive and negative deviations relative to the target glucose value. However, in diabetes management therapy, the risks of hypoglycemia are often a greater concern than hyperglycemia (e.g., because insulin can be delivered to mitigate hyperglycemia but not removed from the body to mitigate hypoglycemia). Accordingly, in exemplary embodiments, an asymmetric cost function is employed to is employed to disproportionately assign a greater cost to negative deviations or excursion in the glucose profile relative to positive deviations. In one or more embodiments, the cost associated with a glucose profile deviating from a target is determined using the natural logarithmic cost function equation (equation 4):

$$f = \frac{\sum_{k=1}^{n} (\log BG_k - \log TG)^2}{n}.$$

Because the natural logarithm of a negative difference is larger than the natural logarithm of a positive difference, the cost function assigns a greater cost to blood glucose samples that are less than the target glucose value. For example, given the same magnitude of deviation ΔG from the target glucose (ΔG=|$BG_k$-TG|), the cost associated with a positive deviation provided by the numerator of the cost function corresponds to (log(TG+ΔG)−log TG)², while the cost associated with a negative deviation provided by the numerator of the cost function corresponds to (log(TG−ΔG)−log TG)². Thus, the cost of a negative deviation from the target will be larger than the cost of a positive deviation. Accordingly, in exemplary embodiments, the personalized updating process 600 utilizes the natural logarithmic cost function to asymmetrically assign a cost to a set of adjusted control parameters (e.g., task 608) and thereby identify a set of adjusted control parameters that minimizes the risks of hypoglycemia (e.g., task 610).

Additionally, or alternatively, in some embodiments, the cost function is designed to minimize the amount of time spent below a hypoglycemic threshold value or other lower threshold glucose value relative to the amount of time spent within a predefined range of glucose values (alternatively referred to as "time in range"). For example, given a series of glucose measurements that make up a simulated glucose profile, the percentage of time spent below a hypoglycemic threshold value or other lower threshold glucose value (e.g., 70 mg/dL) is calculated using the equation:

$$timebelownormal = \frac{\text{total minutes duration of } BG_k < 70}{\text{total minutes duration of } BG_k} * 100.$$

Additionally, the percentage of time spent within a normal range above the lower threshold glucose value but below a hyperglycemic threshold or upper threshold glucose value (e.g., 180 mg/dL) is calculated using the equation:

$$timeinrange = \frac{\text{total minutes duration of } 70 \leq BG_k \leq 180}{\text{total minutes duration of } BG_k} * 100.$$

Thereafter, the percentage spent below the desired range is normalized by the following equation with two factors α and β using the equation:

$$\text{timebelownormal\_normalize} = \frac{timebelownormal}{1 + \alpha e^{-\beta * timebelownormal}}.$$

In this regard, the normalization factors can be adjusted to increase or decrease the cost for violating the hypoglycemic threshold. In an exemplary embodiment, the normalization factors are chosen to be α=100 and β=2 to achieve a desired balance between glucose control efficacy and safety. The final cost can then be determined as a function of the percentage of time spent below the desired range and the time spend within the desired range, either as a function of the normalized percentage of time spent below the hypoglycemic threshold using equation (equation 5):

$$f = \frac{\text{timebelownormal\_normalize}}{5} - \frac{timeinrange}{110},$$

or as a function of the percentage of time spent below the hypoglycemic threshold using equation (equation 6):

$$f = \frac{timebelownormal}{5 * \left(1 + \alpha e^{-\beta * timebelow70}\right)} - \frac{timeinrange}{110}.$$

The number 5 in equations 5 and 6 is a normalization factor representing the ideal maximum for the percentage of time spent below the normal range (e.g., 5%), while the number 110 is a normalization factor chosen to maintain a range for the value of the cost function between −1 and 1 given the maximum percentage for the time in range is 100.

It should be noted that any of the foregoing cost functions could be utilized individually or in combination in connection with the personalized updating process 600 to optimize the personalized control parameter adjustments to achieve a desired minimization of cost. For example, for each set of adjusted parameters, the total cost could be determined as a weighted sum of the cost determined using the natural logarithmic cost function (equation 4) and the cost determined based on the percentage of time spent below range (equation 5 or equation 6), with the weighting factors assigned to different cost functions being chosen to achieve a desired relationship between the magnitude of deviations (equation 4) and the duration of deviations (equation 5 or equation 6). In this regard, the weighting factor assigned to the natural logarithmic cost function may be increased to penalize deviations from the target glucose level, while weighting factor assigned to the time below range cost functions may be increased to penalize prolonged durations below a hypoglycemic threshold. In this regard, there are any number of different manners in which the cost functions (equations 1-6) could be utilized, individually or in combination, to arrive at a total cost determination (e.g., at task 608) that achieves a desired optimization of the personalized control parameter adjustments, and the subject matter described herein is not necessarily intended to be limited to any particular cost function or combination thereof.

For the sake of brevity, conventional techniques related to glucose sensing and/or monitoring, bolusing, closed-loop glucose control, patient modeling, cost functions, optimization and related mathematical concepts, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of automatically adjusting a control parameter for an operating mode of a medical device, the method comprising:
  obtaining, by one or more processors, data pertaining to a physiological condition of a patient during operation of the medical device;
  determining, by the one or more processors, a plurality of adjusted values for the control parameter to be optimized using a cost function based at least in part on the data, the control parameter being a proportional-integral-derivative (PID) gain coefficient value, a PID time constant, an insulin limit, or a pharmodynamical time constant;
  for each of the plurality of adjusted values for the control parameter, determining, by the one or more processors, a respective cost associated with the respective adjusted value for the control parameter based at least in part on the data using the cost function, resulting in a plurality of costs associated with each of the plurality of adjusted values, wherein the cost function disproportionately penalizes negative excursions relative to a target range for the physiological condition, and wherein the cost function disproportionately penalizes the negative excursions relative to the target range by including a first penalty term dependent on time spent outside of the target range, and a second penalty term, different from the first penalty term, dependent on time spent below a lower bound of the target range;
  identifying, by the one or more processors, from among the plurality of adjusted values, an optimized value from among the plurality of adjusted values, wherein the optimized value has a minimum cost associated therewith from among the plurality of costs; and controlling, by the one or more processors, fluid delivery of the medical device to deliver fluid to the patient according to the control parameter at the optimized value.

2. The method of claim 1, wherein:
obtaining the data comprises obtaining measurement data indicative of the physiological condition of the patient; and
determining the plurality of adjusted values for the control parameter comprises adjusting the control parameter based on the measurement data.

3. The method of claim 2, the data including event log data associated with the patient, the method further comprising determining, for each of the plurality of adjusted values for the control parameter, a simulated profile of the physiological condition of the patient based at least in part on the event log data, wherein determining the respective cost associated with the respective adjusted value for the control parameter comprises determining the respective cost associated with the respective adjusted value for the control parameter based at least in part a relationship between the simulated profile associated with the respective adjusted value and a reference value associated with the cost function.

4. The method of claim 3, the reference value comprising a lower threshold value for the physiological condition, wherein determining the respective cost associated with the respective adjusted value for the control parameter comprises determining the respective cost associated with the respective adjusted value for the control parameter based at least in part a percentage of data samples of the simulated profile associated with the respective adjusted value that are below the lower threshold value.

5. The method of claim 1, further comprising determining, for each of the plurality of adjusted values for the control parameter, a simulated profile of the physiological condition of the patient based at least in part on the respective adjusted value and at least some of the data using a digital twin for the patient, wherein determining the respective cost associated with the respective adjusted value for the control parameter comprises determining the respective cost associated with the respective adjusted value for the control parameter based at least in part on relationships between data samples of the simulated profile associated with the respective adjusted value and a reference for the physiological condition.

6. The method of claim 1, further comprising determining, for each of the plurality of adjusted values for the control parameter, a simulated profile of the physiological condition of the patient based at least in part on the respective adjusted value and at least some of the data, wherein determining the respective cost associated with the respective adjusted value for the control parameter is based at least in part on the simulated profile.

7. The method of claim 1, further comprising determining, for each of the plurality of adjusted values for the control parameter, a simulated profile of the physiological condition of the patient based at least in part on the respective adjusted value and at least some of the data, wherein determining the respective cost associated with the respective adjusted value for the control parameter comprises determining the respective cost associated with the respective adjusted value for the control parameter based at least in part on a percentage of data samples of the simulated profile associated with the respective adjusted value that are less than a threshold value.

8. The method of claim 1, wherein updating the control parameter comprises a remote server transmitting the optimized value for the control parameter to the medical device via a network.

9. The method of claim 1, wherein the target range comprises an upper bound and a lower bound different from the upper bound.

10. A patient monitoring system comprising:
a medical device to regulate a physiological condition of a patient in accordance with an operating mode based at least in part on a control parameter; and
a remote device to:
obtain patient data pertaining to operation of the medical device,
determine a plurality of adjusted values for the control parameter to be optimized using a cost function based at least in part on the patient data, the control parameter being a proportional-integral-derivative (PID) gain coefficient value, a PID time constant, an insulin limit, or a pharmodynamical time constant,
determine a respective cost associated with each respective adjusted value of the plurality of adjusted values for the control parameter based at least in part on the patient data using the cost function, resulting in a plurality of costs, wherein the cost function disproportionately penalizes negative excursions relative to a target range for the physiological condition, and wherein the cost function disproportionately penalizes the negative excursions relative to the target range by including a first penalty term dependent on time spent outside of the target range, and a second penalty term, different from the first penalty term, dependent on time spent below a lower bound of the target range,
identify an optimized value having a minimum cost associated therewith from among the plurality of adjusted values based on the plurality of costs, and
control fluid delivery by the medical device to deliver fluid to the patient according to the control parameter at the optimized value.

11. The patient monitoring system of claim 10, the medical device comprising an infusion device to regulate a glucose level of the patient, wherein the remote device determines a simulated glucose profile resulting from each of the plurality of adjusted values based at least in part on the patient data and determines the respective cost associated with each respective adjusted value of the plurality of adjusted values for the control parameter based at least in part on the simulated glucose profile associated with the respective adjusted value.

12. The patient monitoring system of claim 11, wherein the operating mode comprises a closed-loop operating.

13. The patient monitoring system of claim 11, wherein the cost function assigns cost based on a percentage of data samples of the simulated glucose profile that are less than a hypoglycemic threshold.

14. A method of automatically adjusting a control parameter for an operating mode of an infusion device regulating a glucose level of a patient, the method comprising:
obtaining, by one or more processors, patient data comprising sensed glucose measurement data and event log data during a period of operation of the infusion device in accordance with the operating mode;
determining, by the one or more processors, a plurality of adjusted values for the control parameter to be optimized using a cost function based at least in part on the sensed glucose measurement data, the control parameter being a proportional-integral-derivative (PID) gain coefficient value, a PID time constant, an insulin limit, or a pharmodynamical time constant;

for each of the plurality of adjusted values for the control parameter:

determining, by the one or more processors, a simulated glucose profile for the patient corresponding to the period of operation based on the event log data and the respective adjusted value for the control parameter; and determining, by the one or more processors, a respective cost associated with the respective adjusted value for the control parameter based at least in part on the simulated glucose profile using a cost function;

identifying, by the one or more processors, from among the plurality of adjusted values, an optimized value from among the plurality of adjusted values, wherein the optimized value has a minimum cost associated therewith from among a plurality of costs associated with the plurality of adjusted values according to the cost function, wherein the cost function disproportionately penalizes negative excursions relative to a target glucose range, and wherein the cost function disproportionately penalizes the negative excursions relative to the target range by including a first penalty term dependent on time spent outside of the target range, and a second penalty term, different from the first penalty term, dependent on time spent below a lower bound of the target range; and controlling, by the one or more processors, insulin delivery by the infusion device to deliver insulin to the patient according to the control parameter at the optimized value.

15. The method of claim 14, wherein determining the respective cost associated with the respective adjusted value for the control parameter based at least in part on the simulated glucose profile using the cost function comprises determining the respective cost associated with the respective adjusted value for the control parameter based at least in part on a percentage of data samples of the simulated glucose profile that are less than a hypoglycemic threshold.

* * * * *